(12) United States Patent
Pruett (10) Patent No.: US 9,913,702 B1
(45) Date of Patent: Mar. 13, 2018

(54) FLOSSING SYSTEM

(71) Applicant: Timothy J. Pruett, Tavares, FL (US)

(72) Inventor: Timothy J. Pruett, Tavares, FL (US)

( * ) Notice: Subject to any disclaimer, the term of this patent is extended or adjusted under 35 U.S.C. 154(b) by 186 days.

(21) Appl. No.: 15/045,099

(22) Filed: Feb. 16, 2016

(51) Int. Cl.
*A61C 15/00* (2006.01)
*A61C 15/04* (2006.01)

(52) U.S. Cl.
CPC .......... *A61C 15/047* (2013.01); *A61C 15/048* (2013.01)

(58) Field of Classification Search
CPC ..... A61C 15/00; A61C 15/046; A61C 15/047; A61C 15/048
See application file for complete search history.

(56) References Cited

U.S. PATENT DOCUMENTS

| 7,588,035 B2 * | 9/2009 | Ponzini | A61C 15/041 |
| | | | 132/321 |
| 2013/0239986 A1 * | 9/2013 | Pruett | A61C 15/047 |
| | | | 132/309 |

* cited by examiner

*Primary Examiner* — Rachel Steitz

(57) ABSTRACT

A floss arm in a generally cylindrical configuration has a distal end, a proximal end, and an exterior surface there between. The distal end is formed with a distal recess. A replaceable flosser has a central base and two outwardly extending legs. The outwardly extending legs have free ends. A piece of floss is secured between the free ends. The central base is removably received in the distal recess. A floss guard is formed with a center attached to the distal end of the floss arm. A plurality of short arms extend from the center to limit the depth of penetration of the floss. Two laterally spaced long legs extend from the center and span the plurality of short legs to define a central zone for optimal flossing.

10 Claims, 6 Drawing Sheets

FLOSSING SYSTEM

RELATED APPLICATION

The invention of the present application is an improvement over the inventions of my prior applications, application Ser. No. 13/065,228 filed Mar. 17, 2011 which issued Nov. 26, 2013 as U.S. Pat. No. 8,590,546 and application Ser. No. 13/888,335 filed May 6, 2013 which issued Jun. 16, 2015 as U.S. Pat. No. 9,055,991, the subject matter of which applications and patents is incorporated herein by reference.

BACKGROUND OF THE INVENTION

Field of the Invention

The present invention relates to a flossing system and more particularly pertains to cleaning teeth at regions between adjacent teeth of a user and for vibrating regions of the mouth of the user between teeth and gums.

SUMMARY OF THE INVENTION

In view of the disadvantages inherent in the known types of teeth cleaning systems of known designs and configurations now present in the prior art, the present invention provides an improved flossing system. As such, the general purpose of the present invention, which will be described subsequently in greater detail, is to provide a new and improved flossing system and method which has all the advantages of the prior art and none of the disadvantages.

To attain this, the present invention essentially comprises a flossing system. First provided is a floss arm in a generally cylindrical configuration having a distal end and a proximal end and an exterior surface there between. The distal end is formed with a distal recess. A replaceable flosser has a central base and two outwardly extending legs. The legs have free ends with a piece of floss secured between the free ends. The central base is removably received in the distal recess. A floss guard is formed with a center attached to the distal end of the floss arm. A plurality of short arms extend from the center to limit a depth of penetration of the floss. Two laterally spaced long legs extending from the center and span the plurality of short legs.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved flossing system which has all of the advantages of the prior art teeth cleaning systems of known designs and configurations and none of the disadvantages.

It is another object of the present invention to provide a new and improved flossing system which may be easily and efficiently manufactured and marketed for new handles with vibration generating drive mechanisms not currently on the market or otherwise known, existing handles with vibration generating drive mechanisms currently on the market, new handles without vibration generating drive mechanisms not currently on the market, and existing handles without vibration generating drive mechanisms currently on the market.

It is a further object of the present invention to provide a flossing system which is of durable and reliable constructions.

An even further object of the present invention is to provide a new and improved flossing system which is susceptible of a low cost of manufacture with regard to both materials and labor, and which accordingly is then susceptible of low prices of sale to the consuming public, thereby making such flossing system economically available to the buying public.

Lastly, it is an object of the present invention to provide a new and improved flossing system for cleaning teeth at regions between adjacent teeth of a user and for vibrating regions of the mouth of the user between teeth and gums. The cleaning and vibrating is done in a safe, sanitary, painless, convenient, efficient, and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiment and alternate embodiment of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
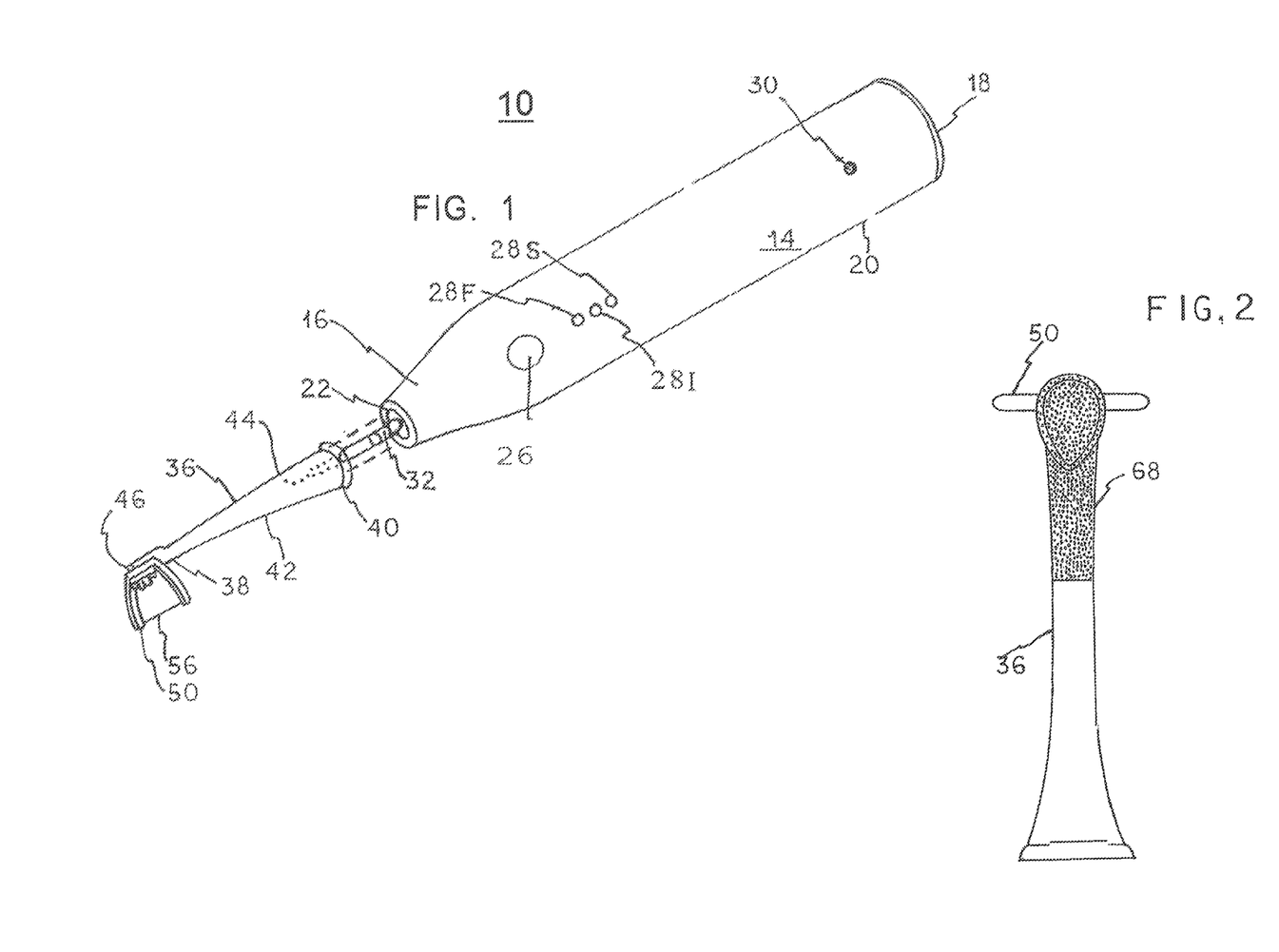
FIG. 1 is an exploded perspective illustration of a flossing system constructed in accordance with the principles of the present invention.
FIG. 2 is a rear elevational view of the flossing system shown in FIG. 1.

With reference now to the drawings, and in particular to FIG. 1 thereof, the preferred embodiment of the new and improved flossing system embodying the principles and concepts of the present invention and generally designated by the reference numeral 10 will be described.

The present invention, the flossing system 10 is comprised of a plurality of components. Such components in their broadest context include a floss arm, a replaceable flosser and a floss guard. Such components are individually configured and correlated with respect to each other so as to attain the desired objective.

More specifically, the present invention is a flossing system 10 for cleaning teeth at regions between adjacent teeth of a user and for vibrating regions of the mouth of the user between teeth and gums. The cleaning and vibrating are done in a safe, sanitary, painless, convenient, efficient, and economical manner.

The system includes a handle 14 in a generally cylindrical configuration. The system has a distal end 16 and a proximal end 18 and an exterior surface 20 between the distal and proximal ends. A vibration generating drive mechanism 22 and a battery are within the handle.

Operational components are provided on the handle. The operational components include an ON/OFF button 26 and an IN-USE light 30 on the exterior surface of the handle. Also included is a low power indicator light 28S which will illuminate when the ON/OFF button is depressed once to vibrate the floss at a slow speed. Also included is an intermediate power indicator light 28I which will illuminate when the ON/OFF button is depressed twice to vibrate the floss at an intermediate speed. Also included is a high power indicator light 28F which will illuminate when the ON/OFF button is depressed three times to vibrate the floss at a fast speed. The operational components also include a vibrating coupler 32 adapted to vibrate rapidly during use upon depressing the ON button.

Figure 10:
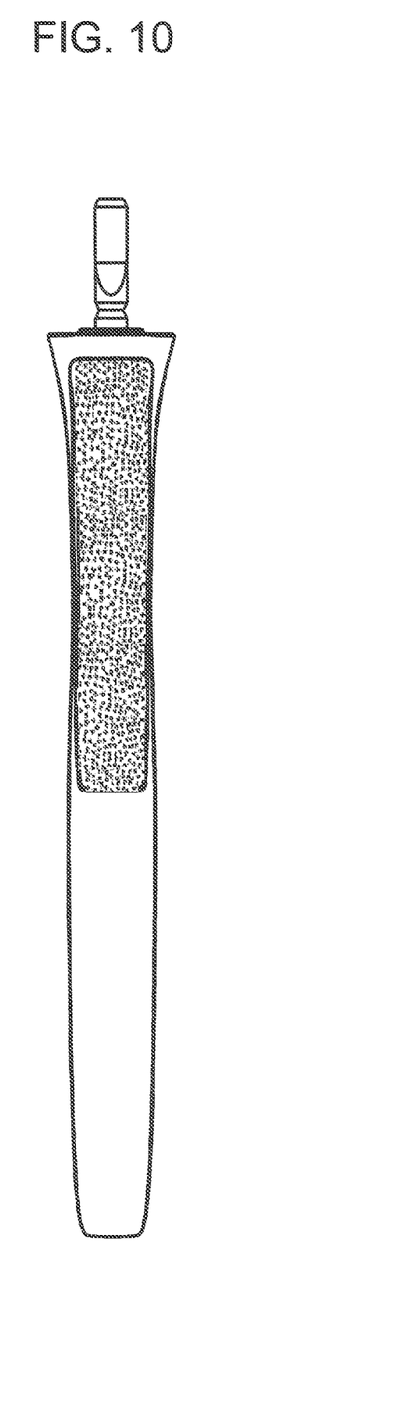
FIG. 10 is a side elevational view of a floss arm coupled with a manual handle without electrical vibrational capabilities.
Figure 11:
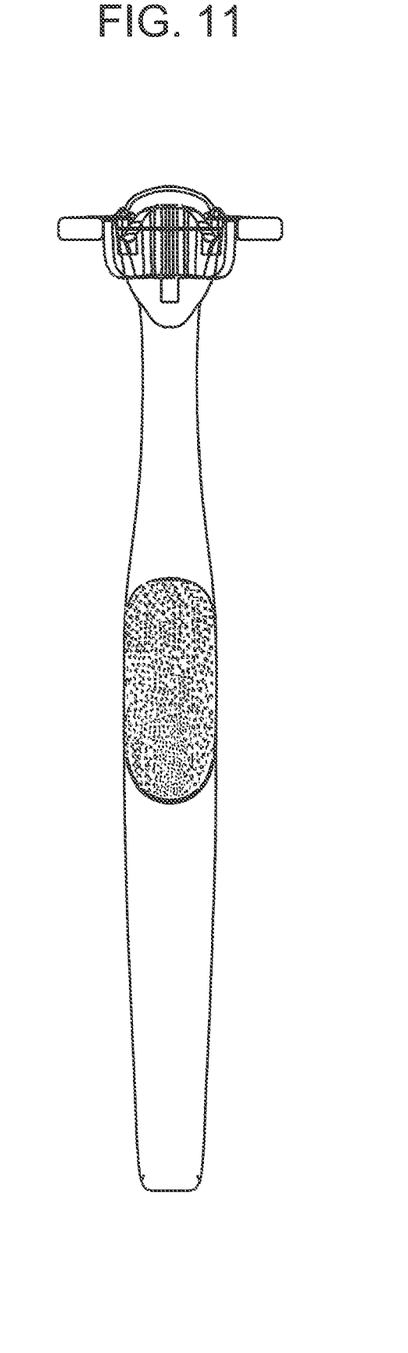
FIG. 11 is an end user product existing as its own handle and provided with a compact flosser.

A floss arm 36 is next provided. The floss arm is in a generally cylindrical configuration and has an enlarged distal end 38 and an enlarged proximal end 40 and an exterior surface 42 between the enlarged distal and enlarged proximal ends. The enlarged proximal end is formed with a proximal recess 44 for receiving the vibrating coupler 32. The enlarged distal end is formed with a planar surface forwardly and a hemispherical surface rearwardly. The hemispherical surface is formed with a transversely extending distal recess 46 in a retentive configuration. The floss arm, if desired, is adapted to be coupled with a manual handle without the electrical vibrational capabilities as illustrated in FIG. 10. The floss arm, if desired, is modifiable to be an end user product existing as its own handle and provided as a compact flosser as illustrated in FIG. 11.

Figures 3, 4:
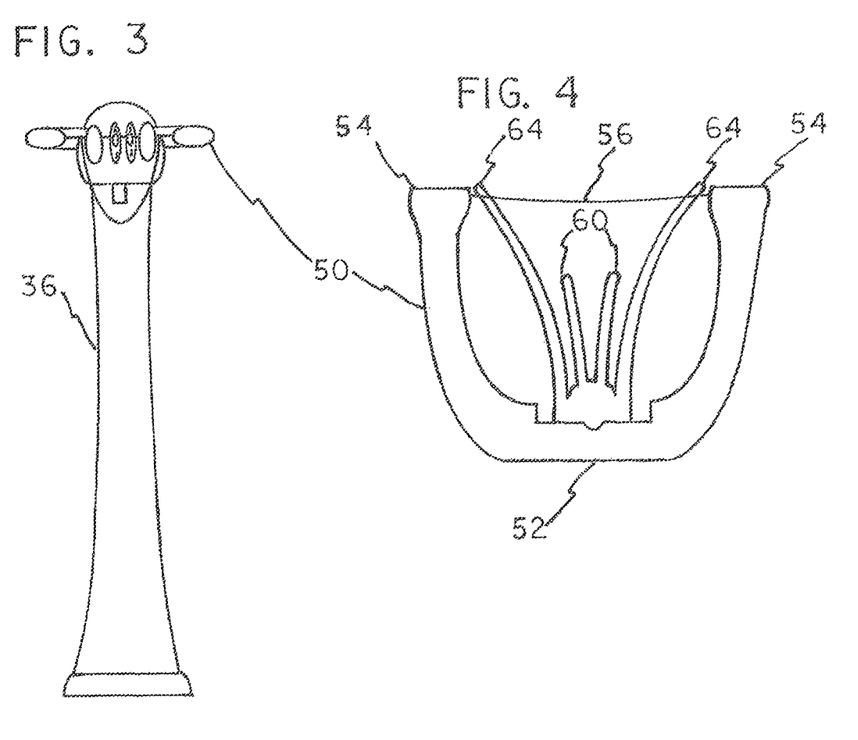
FIG. 3 is a front elevational view of the flossing system shown in FIG. 1.
FIG. 4 is an enlarged front elevational view of the replaceable flosser.
Figure 5:
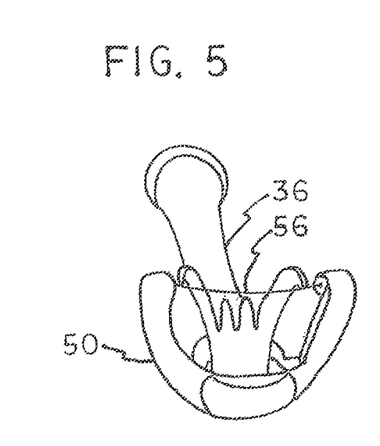
FIG. 5 is a perspective view of the system with the flosser coupled to the floss arm.
Figures 6, 7:
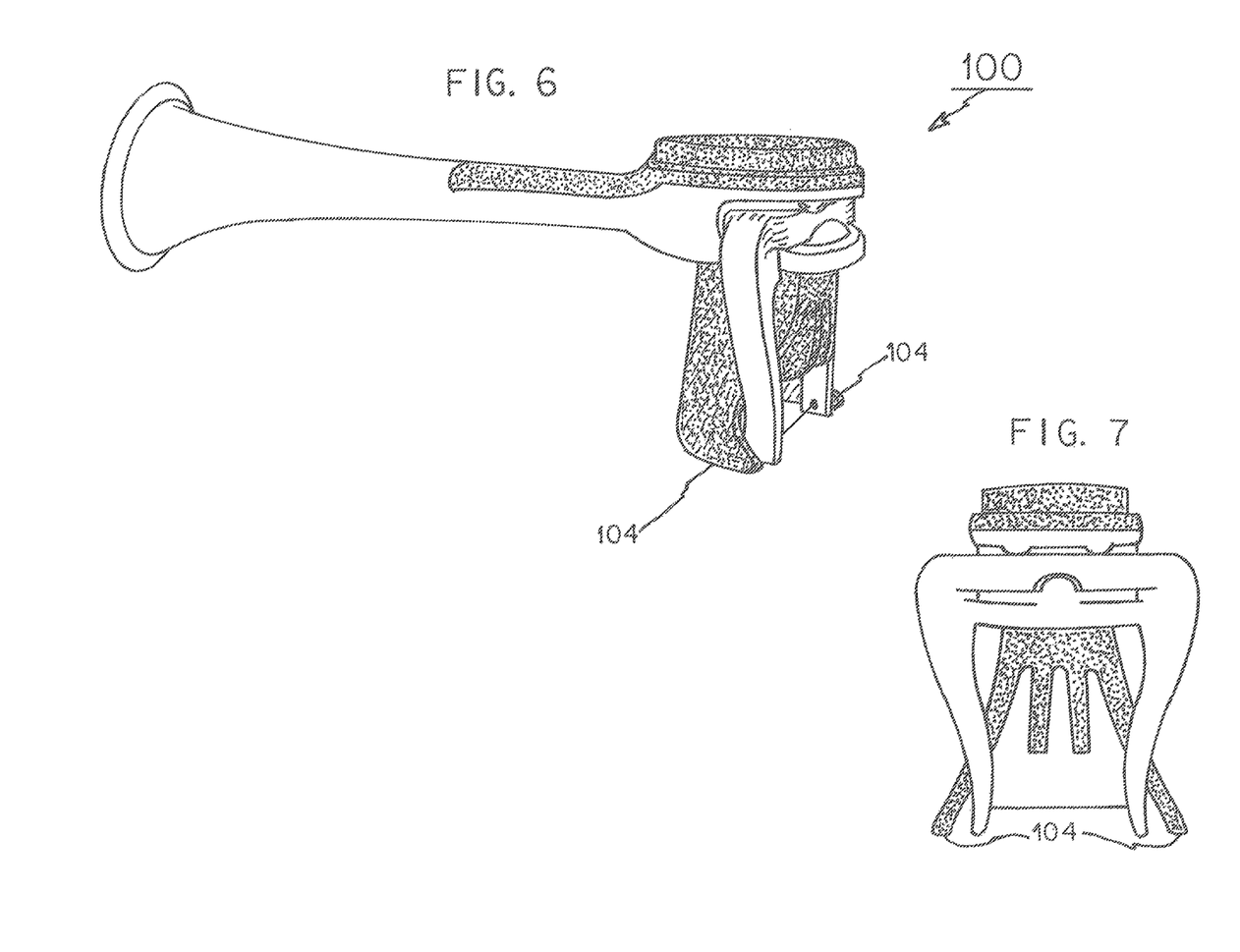
FIG. 6 is a right side perspective view of an alternate embodiment of the invention.
FIG. 7 is a front elevational view of the alternate embodiment of the invention with a replaceable flosser installed on the floss arm.
Figure 8:
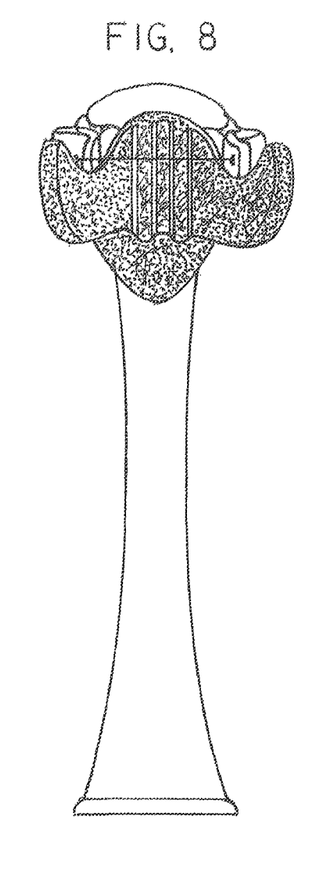
FIG. 8 is a bottom view of the alternate embodiment of the invention with a replaceable flosser installed on the floss arm.
Figure 9:
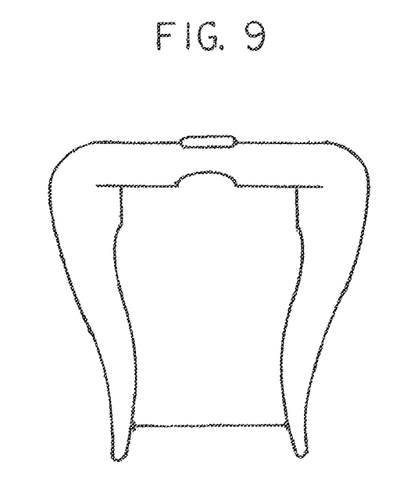
FIG. 9 is a front elevational view of the alternate embodiment of the invention showing the replaceable flosser.

A replaceable flosser 50 has a central base 52 and two outwardly extending legs 54. The central base is removably received in the distal recess. The legs have free ends with a piece of floss 56 secured between the free ends. The central base 52 has a reciprocal retentive shape of the distal recess 46 in which the replaceable flosser is removably received. The floss arm and the replaceable flosser are fabricated of a plastic material with flexibility and resilience whereby applying pressure to the central base of the replaceable flosser toward the distal recess 46 of the floss arm will couple and secure the replaceable flosser with respect to the floss arm. In this manner, applying pressure in an opposite direction to the free ends of the legs will allow uncoupling of the replaceable flosser with respect to the floss arm. The legs are spaced from each other by between 0.50 and 1.00 inches. The floss is fabricated of 100-400 denier ultra high molecular weight polyethylene fiber. The floss is spaced from the base of the replaceable flosser by between 0.25 and 0.75 inches, allowing the teeth to be placed between the legs. The floss is positioned between teeth, thus focusing vibrating energy to effect the flossing as the floss is positioned between the teeth.

Next provided is a floss guard formed with a center and a plurality of short arms 60 extending perpendicular to the floss. The plurality of short arms extend from the center to a location between the legs. The plurality of short arms has a length of between 0.125 and 0.250 inches. The plurality of short arms are adapted to contact the surface of the teeth being flossed to thereby function to control the depth of penetration of the floss between the teeth while the ON button has been depressed and the floss arm is vibrating during flossing or while the floss is positioned with a manual handle using force from the opposing teeth placed on the bite bumper 68.

The floss guard also has two long arms 64 extending outwardly from the center on opposite sides of the plurality of short arms and between the legs. The long arms have inwardly turned terminal ends in contact with the floss adjacent to the legs defining a central zone of the floss between the long arms for optimal flossing, allowing for vertical floss movement and eliminating unwanted and traumatizing lateral floss movement. The replaceable flosser is fabricated of polypropylene and the floss guard is fabricated of a flexible rubber thermoplastic elastomer.

A bite bumper 68 covers the side of the enlarged distal end and a portion of the floss arm there adjacent, the bite bumper being on the exterior surface opposite from the replaceable flosser and the loss guard, the bite bumper being fabricated of soft rubber thermoplastic elastomer.

The releasable coupling between the distal recess 46 and the base 52 of the replaceable flosser 50 is illustrated as being achieved through the fitment of reciprocal retentive shapes. It should be understood, however, that the distal recess and the base of the replaceable flosser could readily take any of a wide variety of complementary configurations whereby they would still achieve their coupling and uncoupling functions.

An alternate embodiment of the invention is illustrated in FIGS. 6 through 9. In such embodiment, the system 100 includes a replaceable flosser with two long arms laterally spaced with outwardly turned terminal ends 104. The terminal ends are located with the two legs and the floss between the long arms to facilitate flossing teeth that have orthodontic braces and wire that normally block the pathway of floss when attempting to use the normal sawing motion with fingers to move floss between teeth. This now becomes possible due to the combination of the narrow flosser legs which fit between orthodontic wire and tooth, the ability to move floss between teeth using force applied to the bite bumper by opposing teeth, and controlling the depth and lateral position of the floss with the floss guard to eliminate the potential for gum or tooth trauma.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A flossing system comprising:
   a floss arm in a generally cylindrical configuration having a distal end (38) and a proximal end and an exterior surface there between, the distal end being formed with a distal recess (46);
   a replaceable flosser having a central base and two outwardly extending legs, the legs having free ends with a piece of floss secured between the free ends, the central base being removably received in the distal recess; and
   a floss guard formed with a center attached to the distal end of the floss arm, a plurality of short arms extending from the center to limit a depth of penetration of the floss, two laterally spaced long legs extending from the center and spanning the plurality of short legs, and a plurality of long arms (64) having inwardly turned terminal ends contacting the floss to define a central zone for optimal flossing.

2. The system as set forth in claim 1 wherein the floss is fabricated of 100-400 denier ultra high molecular weight polyethylene.

3. The system as set forth on claim 1 wherein the replaceable flosser is fabricated of polypropylene and the floss guard is fabricated of flexible rubber thermoplastic elastomer.

4. The system as set forth in claim 1 and further including:
   a bite bumper on the distal end remote from the replaceable flosser and the floss guard.

5. The system as set forth in claim 4 wherein the bite bumper is fabricated of a soft rubber thermoplastic elastomer.

6. The system as set forth in claim 4 and further including:
   a non-electric handle coupled to the floss arm for manually positioning the flossing system to utilize the floss guard and bite bumper.

7. The system as set forth in claim 4 and further including:
   a non-electric compact extension of the floss arm for manually positioning the flossing system to utilize the floss guard and bite bumper.

8. The system as set forth in claim 1 and further including:
   a handle coupled to the floss arm with electrical components to vibrate the floss, the replaceable flosser and the floss guard being fabricated of a flexible plastic material.

9. A flossing system comprising:
   a floss arm in a generally cylindrical configuration having a distal end (38) and a proximal end and an exterior surface there between, the distal end being formed with a distal recess (46);
   a replaceable flosser having a central base and two outwardly extending legs, the legs having free ends with a piece of floss secured between the free ends, the central base being removably received in the distal recess; and
   a floss guard formed with a center attached to the distal end of the floss arm, a plurality of short arms extending from the center to limit a depth of penetration of the floss, two laterally spaced long legs extending from the center and spanning the plurality of short legs, and a plurality of long arms having laterally spaced, outwardly turned terminal ends (104) located with the two legs and the floss between the long arms to facilitate flossing teeth that have braces.

10. A flossing system (10) for cleaning teeth at regions between adjacent teeth of a user and for vibrating regions of the mouth of the user between teeth and gums, the cleaning and vibrating being done in a safe, sanitary, painless, convenient, efficient, and economical manner, the system consisting of:
   a handle (14) in a generally cylindrical configuration and having a distal end (16) and a proximal end (18) and an exterior surface (20) between the distal and proximal ends, a vibration generating drive mechanism (22) and a battery within the handle;
   operational components on the handle, the operational components including an ON button (26) and an OFF button (28) and an IN-USE light (30) on the exterior surface of the handle adjacent to the distal end, the operational components also including a vibrating coupler (32) adapted to vibrate rapidly during use upon depressing the ON button;
   a floss arm (36) in a generally cylindrical configuration and having an enlarged distal end (38) and an enlarged proximal end (40) and an exterior surface (42) between the enlarged distal end and the enlarged proximal end, the enlarged proximal end being formed with a proximal recess (44) for receiving the vibrating coupler (32), the enlarged distal end being formed with a planar surface forwardly and a hemispherical surface rearwardly, the hemispherical surface being formed with a transversely extending distal recess (46) in a retentive configuration;
   a replaceable flosser (50) having a central base (52) and two outwardly extending legs (54), the central base removably received in the distal recess, the legs having free ends with a piece of floss (56) secured between the free ends, the central base (52) having the reciprocal retentive shape of the rearwardly facing transverse distal recess (46) to which the replaceable flosser will be removably received, the floss arm and the replaceable flosser being fabricated of a plastic material with flexibility and resilience whereby applying pressure to the central base of the replaceable flosser toward the retentive distal recess (46) of the floss arm will couple and secure the replaceable flosser with respect to the floss arm and whereby applying pressure in an opposite direction to the free ends of the legs will allow uncoupling of the replaceable flosser with respect to the floss arm, the legs being spaced from each other by between 0.50 and 1.00 inches, the floss being fabricated of 100-400 denier ultra high molecular weight polyethylene fiber, the floss being spaced from the base of the replaceable flosser by between 0.25 and 0.75 inches, allowing the teeth to be placed between the legs, and allowing the floss to be positioned between teeth, whereby vibrating energy is focused to effect flossing; and a floss guard including a center and a plurality of short arms (60) perpendicular to the floss, the short arms extending from the center and extending between the legs, the short arms having a length of between 0.125 and 0.250 inches, the short arms being adapted to contact the surface of the teeth being flossed to thereby function to control the depth of penetration of the floss between the teeth while the ON button has been depressed and the floss arm is vibrating during flossing;

the floss guard also including two long arms (64) extending outwardly from the center on opposite sides of the short arm and between the legs, the long arm having inwardly turned terminal end in contact with the floss adjacent to the leg defining a central zone on the floss for optimal flossing, the floss guard being fabricated of a flexible rubber thermoplastic elastomer and the replaceable flosser being fabricated of polypropylene; and a bite bumper (68) covering the side of the enlarged distal end and a portion of the floss arm there adjacent, the bit bumper being on the exterior surface opposite from the replaceable flosser and the floss guard, the bite bumper being fabricated of soft rubber thermoplastic elastomer.

\* \* \* \* \*